United States Patent [19]

Shepherd

[11] Patent Number: 5,415,642
[45] Date of Patent: May 16, 1995

[54] CATHETER COVER

[76] Inventor: Brad Shepherd, 3335 E. Miraloma, #141, Anaheim, Calif. 92806

[21] Appl. No.: 191,513

[22] Filed: Feb. 3, 1994

[51] Int. Cl.⁶ ............................................. A61M 27/00
[52] U.S. Cl. .................................... 604/344; 604/180; 604/355; 128/DIG. 26
[58] Field of Search ................... 128/206.14, DIG. 26, 128/887, 846, 856, 888; 604/180, 174, 163, 171, 263, 355, 344, 327, 332; 602/901, 41, 54

[56] References Cited

U.S. PATENT DOCUMENTS

| | | |
|---|---|---|
| 2,898,917 | 8/1959 | Wallace . |
| 3,194,235 | 7/1965 | Cooke . |
| 3,604,421 | 9/1971 | Pizzella ............................... 604/344 |
| 3,782,377 | 1/1974 | Rychlik . |
| 4,059,105 | 11/1977 | Cutruzzula et al. . |
| 4,224,937 | 9/1980 | Gordon . |
| 4,553,967 | 11/1985 | Ferguson et al. ..................... 604/344 |
| 4,667,666 | 5/1987 | Fryslie . |
| 4,681,574 | 7/1987 | Eastman ............................... 604/344 |
| 4,929,236 | 5/1990 | Sampson . |
| 5,086,763 | 2/1992 | Hathman . |
| 5,144,958 | 9/1992 | Krueger et al. . |
| 5,248,307 | 9/1993 | Sokoloff .............................. 128/846 |

FOREIGN PATENT DOCUMENTS 3105187 9/1982 Germany .
2147811 5/1985 United Kingdom .

Primary Examiner—John G. Weiss
Attorney, Agent, or Firm—Knobbe, Martens, Olson & Bear

[57] ABSTRACT

Disclosed is a fluid-impermeable protective shield for covering the proximal end of an indwelling, percutaneous catheter and the puncture site through which the catheter extends. A medical grade adhesive is used to attach the protective shield to the skin that surrounds the puncture site. The protective shield allows the patient to swim or bathe without undue risk of infection.

18 Claims, 2 Drawing Sheets

CATHETER COVER

FIELD OF THE INVENTION

The present invention relates to the use of an indwelling, percutaneous catheter. More particularly, the present invention relates to a protective shield for maintaining a clean environment around the percutaneous puncture site of an indwelling catheter.

BACKGROUND OF THE INVENTION

For a variety of medical ailments it is desirable to leave a catheter in place within a patient for an extended period of time. A catheter may be left in place, for example, to permit periodic blood transfusions, to perform renal dialysis, or to permit the periodic administration of antibiotics, chemotherapy treatment, or TPN (total parenteral nutrition).

The type of indwelling catheter used is dictated by a variety of circumstances such as the condition being treated, individual patient characteristics and requirements, and the expected duration for which the catheter will remain in place. Under certain circumstances, it is desirable to use a catheter such as a PORT-A-CATH that is completely embedded under the skin. This type of catheter can be accessed periodically by inserting a needle through the skin and into an access port of the catheter. The risk of infection is relatively low for this type of catheter since no portion of the catheter resides outside of the body, and since no puncture site is required when the catheter is not being accessed.

For some applications in which the catheter will remain in place for a relatively short term, it is often desirable to use a percutaneous catheter. This type of catheter has a distal end that is located inside the body (for example, within the superior vena cava in patients being treated for certain types of cancer) and a proximal end that is located outside the body.

Indwelling, percutaneous catheters have the disadvantage of extending through a puncture site which can serve as a portal for infectious agents such as bacteria, fungi and viruses to enter into the system. Patients that use this type of catheter must, therefore, take extraordinary precautions to keep the proximal end of the catheter and the region surrounding puncture site in a clean condition. In particular, such patients typically must refrain from swimming, showering and similar contacts with fluids. There is therefore a need to provide a means for shielding both the proximal end of a percutaneous catheter and the puncture site from fluids or other media that may contain infectious agents.

SUMMARY OF THE INVENTION

The present invention provides a protective shield for maintaining a clean environment around the proximal extension of an indwelling catheter and its percutaneous puncture site. In accordance with one embodiment of the invention, the protective shield comprises a fluid-impermeable housing that has an open end and a closed end. The housing is preferably composed of a flexible material that is substantially impervious to infectious agents. The housing has base at its open end. The base is preferably in the form of a flexible rim or flange that extends in an outward direction from the open end of the housing to define a bottom surface. A medical grade adhesive is disposed upon the bottom surface of the base, allowing the protective shield to be attached to the skin that surrounds the puncture site. The housing has a sufficient interior volume to receive the proximal extension of the indwelling catheter.

A significant feature of the present invention is that the protective shield constructed in accordance with the invention provides a fluid-impermeable seal when applied to a patient. The protective shield thereby isolates the puncture site and the proximal end of the catheter from potentially harmful fluids, allowing the patient to swim or bathe while minimizing the risk of infection.

Also provided in accordance with the present invention is a method for maintaining a clean environment around the percutaneous puncture site of an indwelling catheter. The method involves the steps of identifying the entry site of the catheter, advancing the proximal end of the catheter through the open end of the housing and into a chamber portion, and securing the base of the housing to the skin of the patient. The base is applied to the skin in a manner that surrounds the puncture site.

Further objects, features and advantages of the present invention will become apparent from the detailed description which follows, when considered together with the attached drawings and claims.

DETAILED DESCRIPTION OF PREFERRED EMBODIMENTS

Figure 1:
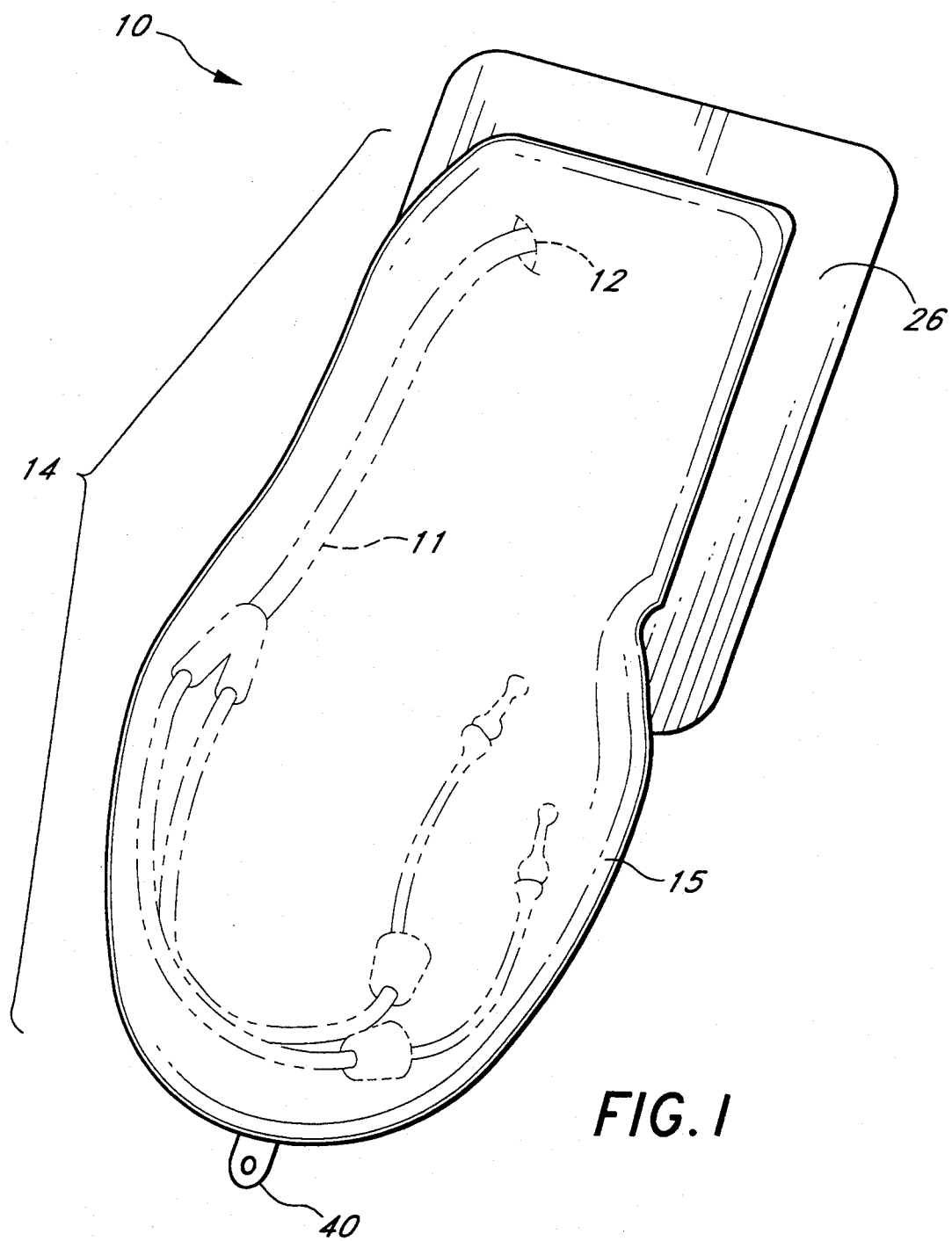
FIG. 1 is a perspective view of a catheter cover according to one embodiment of the present invention. In this view the proximal end of a catheter is shown in phantom protruding from a puncture site in the skin.

FIG. 1 illustrates a catheter cover 10 according to one embodiment of the present invention. The catheter cover 10 is shown as covering the proximal end of a catheter 11 (shown in phantom) that protrudes from a puncture site 12 in the skin of a patient. The catheter cover 10 comprises a housing 14 that encloses the proximal end of the catheter 11. The housing 14 comprises a wall 15 that is composed of a flexible, fluid-impermeable material that is preferably substantially impervious to bacterium, fungi, viruses and other infectious agents. Various materials such as latex and silicone rubber are available for this purpose, as will be appreciated by one skilled in the art.

Figure 2:
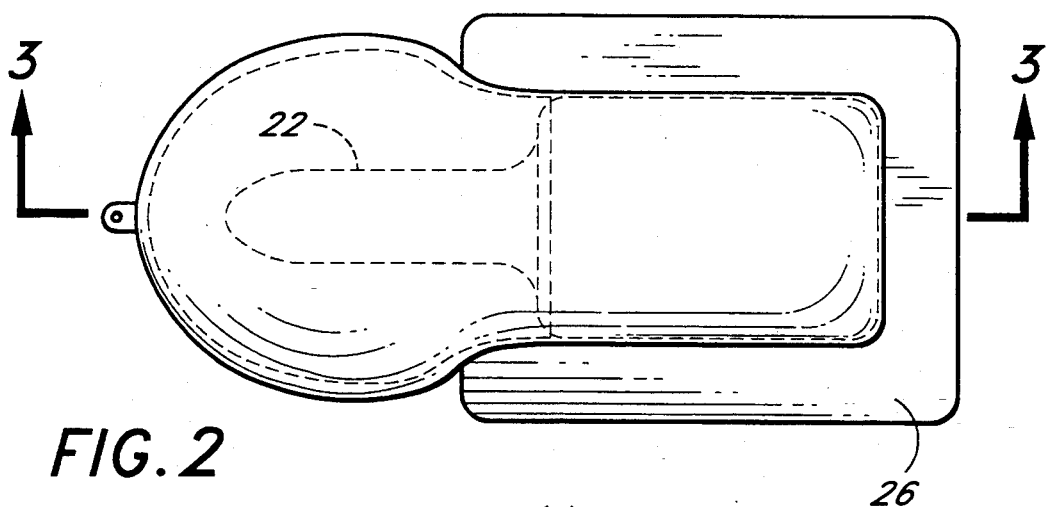
FIG. 2 is a top plan view of a catheter cover of the present invention.
Figure 3:
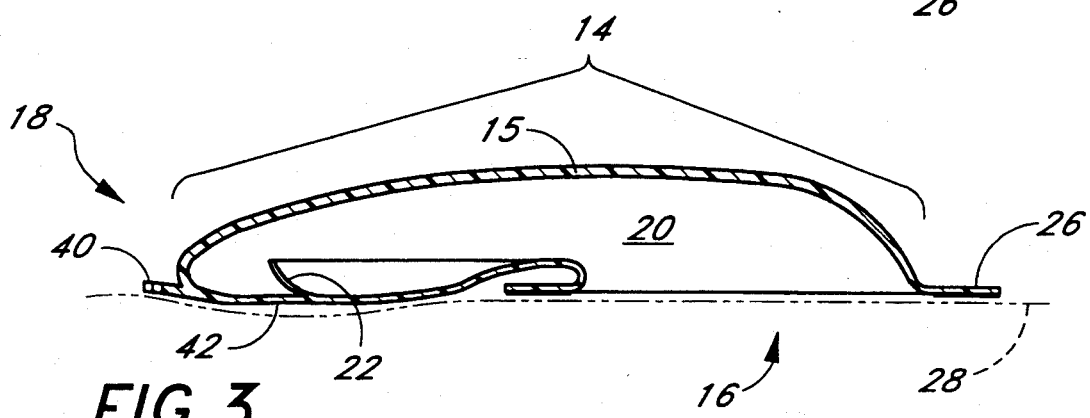
FIG. 3 is an elevational partial cross-sectional view taken along the line 3—3 of FIG. 2.

Referring to FIG. 3, the housing 14 has an open end 16 and a closed end 18. The open end 16 allows a catheter to be received into a chamber 20 formed by the inner surface of the wall 15. Attached to the inner surface of the wall 15 there is optionally provided a catheter retention structure such as a rib 22 (also shown in phantom in FIGS. 2 and 4). The rib 22 serves to impede undesired movement of the proximal end of a catheter that is housed within the chamber 20. To perform this function, the catheter can be inserted such that it passes between the periphery of the rib 22 (best seen in FIG. 2) and the wall 15 at the closed end 18 of the housing 14. Any of a variety of alternative retention structures can readily be provided by one of skill in the art in view of the disclosure herein.

Referring primarily to FIGS. 1 and 3, the housing 14 has a base 26. The base 26 is preferably in the form of an annular ring or flange that extends radially outwardly from the wall 15 of the housing 14 with respect to the plane of the open end 16. The base 26 preferably comprises a fluid-impermeable material which may or may not be the same material used for the housing 14. Alternatively, the base may comprise a vapor permeable material in embodiments intended for relatively long-term adhesion to the skin. The base 26 is preferably composed of a flexible material capable of conforming to the contour of the skin 28 (shown in phantom in FIG. 3).

Figure 4:
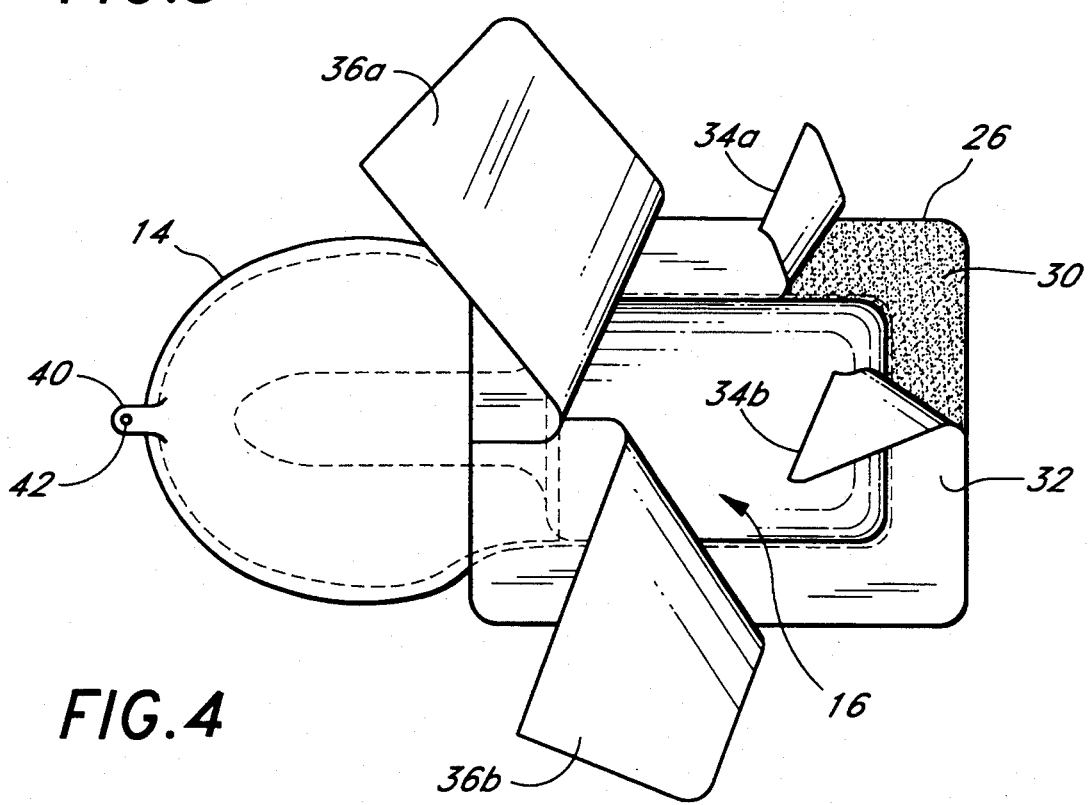
FIG. 4 is a bottom plan view of the catheter cover of the present invention, showing release layers partially removed.

Referring to FIG. 4, the bottom surface of the base 26 is provided with an adhesive surface suitable for application to the skin 28. The adhesive 30 is preferably applied around the entire bottom surface of the base 26 without discontinuity so that a protective seal can be formed when the base 26 is applied to the skin.

Base 26 may be constructed in any of a variety of manners that accomplishes the function of adhering the wall 15 to the skin in a manner that substantially prevents entry of water. For example, base 26 may comprise an annular flange that is integrally molded with the remainder of wall 15. The adhesive coating is applied to the bottom surface of the base 26 in accordance with any of a variety of conventional techniques. Alternatively, the base 26 comprises one or more additional support layers to produce a laminate or sandwich configuration for imparting increased structural integrity compared to the remainder of wall 15.

In an alternate embodiment the wall 15 is formed with an annular flange, substantially as shown in FIG. 3. As used herein, "annular" refers to a closed geometric configuration that completely surrounds the opening 16. The use of "annular" is not intended to imply any particular configuration, such as circular, oval, rectangular, square, or other, as may be desired for a particular embodiment of the present invention. Although the illustrated embodiment is provided with a generally rectangular or nearly square base 26, that is merely for the purpose of illustrating a particular embodiment.

In one embodiment, a support layer having a central aperture for receiving the housing 14 is provided, having an annular configuration that corresponds to the configuration of the annular flange. The support layer is preferably provided with an adhesive surface on its lower side, so that it can be advanced over the housing 14 and applied to the top of the annular flange 26. The support layer in one embodiment extends radially outwardly beyond the limit of flange 26, so that the adhesive surface of the support layer both adheres to the top of the annular flange 26 and also to the skin of the patient. Any of a variety of other fabricated or laminated configurations for adhering the housing 14 to the skin can readily be devised by one of skill in the art in view of the disclosure herein.

The adhesive 30 is shown in FIG. 4 as being covered by a release layer 32 (shown as partially peeled away). Release layer 32 allows the proximal end of a catheter to be inserted within the housing 14 without sticking to the adhesive 30. Release layer 32 is shown as having a slit that forms two edges 34a and 34b. Edges 34a and 34b adjoin when the release layer 32 fully covers the adhesive 30. The slit allows the release layer 32 to easily be removed after the proximal end of a catheter has been inserted within the housing 14. Other release layer configurations can also readily be devised by one of skill in the art.

The release layer 32 is shown in FIG. 4 as being partially covered by two additional protective peels 36a and 36b (shown as partially peeled away). Protective peels 36a and 36b releasably adhere to the bottom surface of release layer 32. Prior to removal, protective peels 36a, 36b cover the open end 16 of the housing 14, thereby maintaining the chamber 20 in a substantially sterile condition. Other configurations of the protective peel 36a and 36b, such as the use of only a single protective peel to cover the entire base of the device, can readily be used, as will be appreciated by one of skill in the art.

It has been determined by the inventor herein that the use of the protective catheter cover of the present invention with catheters having relatively long, proximal extensions protruding from the skin can, upon normal movement of the patient, place undue strain upon the seal provided between the adhesive 30 and the patient's skin. In order to minimize the likelihood of inadvertent removal of the catheter cover 10, one or more structures are preferably provided to immobilize the closed end 18 of the housing 14.

Referring primarily to FIGS. 3 and 4, one or more anchoring tabs 40 are optionally provided at the exterior surface of the housing 14. Anchoring tab 40 is preferably attached to the wall 15 in the region of the closed end 18 as shown. Anchoring tab 40 provides a means for anchoring the housing to the skin or clothing of the patient by any of a variety of anchoring or fastening means. The tab 40 optionally has an adhesive backing or hole 42 punched through it to allow a safety pin or other fastening device to easily be attached to the tab 40.

Alternatively, referring to FIG. 3, skin contact surface 42 on the housing 14 may be provided with an adhesive coating (not illustrated) beneath a second release layer or a continuation of the release layer 32 previously discussed. The provision of an adhesive on surface 42 can be used alone or in combination with one or more anchors 40.

To use the catheter cover 10, the protective peels 36a, 36b are initially removed and the proximal end of the catheter is inserted within the housing 14. Protective peel 32 is then removed from the bottom surface of the base 26 to expose the adhesive 30. The base 26 is then applied to the skin 28 such that the bottom surface of the base 26 surrounds the puncture site 12 (FIG. 3). Depending upon the manner in which the closed end 18 of the housing 14 is immobilized, the base 26 may be applied to the skin 28 such that the closed end 18 of the housing 14 "hangs" at a vertically lower position than the base 26.

For embodiments of the catheter cover 10 that include the rib 22, the catheter can be positioned around the rib 22 by applying force to the exterior surface of the wall 15. For embodiments of the catheter cover that include the anchoring tab 40, the catheter cover can be anchored to the skin 28 using tape, or can be anchored to the interior or exterior surface of clothing using a suitable fastening device. The weight of the catheter 11 can thereby be offset to reduce the degree to which the base 26 pulls on the skin 28. Use of the anchoring tab 40 also reduces the likelihood that the catheter cover 10 will catch on a foreign object and be pulled from the skin 28.

Once applied to the skin 28, the catheter cover 10 provides a protective, fluid-impermeable shield for the puncture site 12 (FIG. 1) and the proximal end of the catheter 11. The catheter cover 10 thereby allows the patient to swim, bathe, etc. without undue risk of infection.

It is contemplated that the catheter cover 10 as described will be sold in individually wrapped, sterile packages that can be opened immediately prior to use. It is further contemplated that the catheter cover 10 will be sold as a relatively inexpensive, one-time-use disposable product.

It should be understood that a catheter cover in accordance with the present invention can be used with virtually any type of device that passes through the skin, such as to permit the passage of fluids, electrical currents, and the like. Thus, the terms "catheter" and "indwelling catheter," as used herein to describe the present invention, are intended to include all devices that meet this description.

Although this invention has been described in terms of certain preferred embodiments, other embodiments that are apparent to those or ordinary skill in the art are also within the scope of this invention. Accordingly, the scope of the present invention is intended to be defined only by reference to the appended claims.

What is claimed is:

1. A protective shield for maintaining a clean environment around the percutaneous puncture site of a catheter, comprising:
    a fluid-impermeable housing for receiving the proximal end of a catheter projecting through the skin, said housing having at least one open end;
    a catheter retention structure attached to an internal surface of said housing;
    a base for contacting the skin, said base surrounding an open end of said housing; and
    an adhesive on a bottom surface of said base, for attaching said base to the skin.

2. A protective shield as in claim 1, wherein said housing is substantially impervious to bacteria, fungi and viruses.

3. A protective shield as in claim 1, wherein said housing comprises latex.

4. A protective shield as in claim 1, wherein said base comprises an annular flange integrally formed with said open end of said housing.

5. A protective shield as in claim 1, further comprising at least one anchoring tab attached to an outer surface of said housing.

6. A protective shield as in claim 1, wherein said adhesive is a medical grade adhesive suitable for application to the skin.

7. A protective shield as in claim 1, wherein said retention structure is a rib for impeding the motion of the proximal end of a catheter.

8. A method of inhibiting contamination of a catheter entry site on a patient, comprising the steps of:
    identifying an entry site of a catheter, said catheter having a distal end inside the body of a patient and a proximal end projecting through the entry site and out of the body of the patient;
    advancing the proximal end of the catheter into a chamber of a protective shield, said protective shield having a base, said base having an adhesive on a bottom surface;
    securing the base to the skin of the patient such that the base surrounds the entry site and the proximal end of the catheter is fully contained within the protective shield; and
    anchoring said protective shield to the clothing of the patient.

9. A protective shield for maintaining a clean environment around the percutaneous puncture site of a catheter, comprising:
    a fluid-impermeable housing for receiving the proximal end of a catheter projecting through the skin, said housing having at least one open end;
    means for maintaining a chamber region of said housing in a substantially sterile condition prior to use;
    a base for contacting the skin, said base surrounding an open end of said housing;
    an adhesive on a bottom surface of said base, for attaching said base to the skin; and
    a catheter retention structure attached to an internal surface of said housing.

10. A protective shield as in claim 9, wherein said retention structure is a rib for impeding the motion of the proximal end of a catheter.

11. A protective shield as in claim 9 wherein said housing is substantially impervious to bacteria, fungi and viruses.

12. A protective shield as in claim 9, wherein said housing comprises latex.

13. A protective shield as in claim 9, wherein said base comprises an annular flange integrally formed with said open end of said housing.

14. A protective shield as in claim 9, further comprising at least one anchoring tab attached to an outer surface of said housing.

15. A protective shield as in claim 9, wherein said adhesive is a medical grade adhesive suitable for application to the skin.

16. A protective shield as in claim 9, wherein said means for maintaining a chamber region of said housing in a substantially sterile condition comprises a protective peel that covers said open end of said housing.

17. A protective shield as in claim 9, wherein said means for maintaining a chamber region of said housing in a substantially sterile condition comprises a sterile package.

18. A method of inhibiting contamination of a catheter entry site on a patient, comprising the steps of:
    identifying an entry site of a catheter, said catheter having a distal end inside the body of a patient and a proximal end projecting through the entry site and out of the body of the patient;
    inhibiting contamination of the entry site, said inhibiting step comprising advancing the proximal end of the catheter into an opening in a catheter receiving chamber of a protective shield, said protective shield having a base surrounding said opening, said base having an adhesive on a bottom surface, and securing the base to the skin of the patient such that the base surrounds the entry site and the proximal end of the catheter is fully contained within the protective shield; and
    anchoring said protective shield to the patient.

* * * * *